United States Patent
Young

(10) Patent No.: US 7,641,674 B2
(45) Date of Patent: Jan. 5, 2010

(54) DEVICES FOR SECURING ELONGATED SPINAL CONNECTING ELEMENTS IN BONE ANCHORS

(75) Inventor: Stewart Young, Memphis, TN (US)

(73) Assignee: Warsaw Orthopedic, Inc.

( * ) Notice: Subject to any disclaimer, the term of this patent is extended or adjusted under 35 U.S.C. 154(b) by 133 days.

(21) Appl. No.: 11/365,710

(22) Filed: Mar. 1, 2006

(65) Prior Publication Data

US 2007/0208344 A1 Sep. 6, 2007

(51) Int. Cl.
*A61B 17/70* (2006.01)

(52) U.S. Cl. .................. 606/270; 606/264; 606/267; 411/393

(58) Field of Classification Search ............... 623/17.11, 623/17.12, 17.13, 17.14, 17.15, 17.16; 411/393, 411/427, 5; 606/72, 73, 61, 254, 255, 256, 606/257, 258, 259, 260, 261, 262, 263, 264, 606/265, 266, 267, 268, 269, 270, 271, 272, 606/273, 274, 275, 276, 277, 278, 279, 300, 606/301, 302, 303, 304, 305, 306, 307, 308, 606/309, 310
See application file for complete search history.

(56) References Cited

U.S. PATENT DOCUMENTS

| | | | | |
|---|---|---|---|---|
| 2,927,332 A | * | 3/1960 | Moore | 470/8 |
| 3,419,058 A | * | 12/1968 | Walker | 411/168 |
| 4,304,424 A | * | 12/1981 | Hansen | 285/111 |
| 4,538,947 A | * | 9/1985 | Burkholder | 411/393 |
| 4,764,068 A | * | 8/1988 | Crispell | 411/393 |
| 5,005,562 A | * | 4/1991 | Cotrel | 606/61 |
| 5,073,074 A | | 12/1991 | Corrigan et al. | |
| 5,667,508 A | | 9/1997 | Errico et al. | |
| 5,697,929 A | | 12/1997 | Mellinger | |
| 5,885,286 A | * | 3/1999 | Sherman et al. | 606/61 |
| 6,004,349 A | | 12/1999 | Jackson | |
| 6,056,753 A | * | 5/2000 | Jackson | 606/73 |
| 6,261,288 B1 | * | 7/2001 | Jackson | 606/61 |
| 6,296,642 B1 | * | 10/2001 | Morrison et al. | 606/61 |
| 6,565,565 B1 | * | 5/2003 | Yuan et al. | 606/61 |
| 6,786,903 B2 | * | 9/2004 | Lin | 606/23 |
| 6,843,791 B2 | | 1/2005 | Serhan | |
| 7,141,051 B2 | * | 11/2006 | Janowski et al. | 606/61 |
| 7,204,838 B2 | * | 4/2007 | Jackson | 606/61 |
| 2001/0047208 A1 | * | 11/2001 | Michelson | 623/17.16 |
| 2002/0120272 A1 | * | 8/2002 | Yuan et al. | 606/61 |
| 2004/0039383 A1 | | 2/2004 | Jackson | |
| 2004/0153068 A1 | * | 8/2004 | Janowski et al. | 606/61 |

FOREIGN PATENT DOCUMENTS

EP 0 348 272 A1 12/1989
WO WO 00/27297 5/2000

* cited by examiner

*Primary Examiner*—Eduardo C Robert
*Assistant Examiner*—Jan Christopher Merene

(57) ABSTRACT

Devices and methods include an anchor assembly engageable to a vertebra and a connecting element positionable through a receiver of the anchor assembly. The assembly includes an engaging member for engaging the connecting element in the receiver. The engaging member includes a plurality of elongated arcuate projecting members extending about a rotational center of the engaging member and projecting from an end surface of the engaging member to positively engage the connecting element in the receiver.

19 Claims, 3 Drawing Sheets

DEVICES FOR SECURING ELONGATED SPINAL CONNECTING ELEMENTS IN BONE ANCHORS

BACKGROUND

Elongated connecting elements, such as rods, plates, tethers, wires, cables, and other devices have been implanted along the spinal column and connected between two or more bone anchors engaged between one or more spinal motion segments. Such connecting elements can be positioned in the respective bone anchors with a top-down approach, a side-to-side approach, or a serial, endwise approach. In any event, it is desirable to securely engage the connecting element in the bone anchor to maintain the spinal stabilization effect provided by the connecting element when engaged between the bone anchors.

Set screws, nuts, caps, and other engaging members can be engaged to the bone anchor to maintain the connecting element therein. However, it can be desirable to enhance the engagement relationship between the engaging member and connecting element to prevent or resist movement of the connecting element relative to the bone anchor. In addition, enhancement of the engagement of the engaging member with the connecting element can prevent the engaging member from "backing out" or loosening from the bone anchor after engagement thereto.

SUMMARY

The present invention generally relates to devices and methods that securely engage an elongated connecting element in a receiver of an anchor assembly. The anchor assembly includes an anchor member engageable to bony structure and the receiver includes a passage for receiving the connecting element when the connecting element is positioned along the bony structure. The anchor assembly includes an engaging member that engages the receiver and the connecting element to secure the connecting element in the receiver.

According to one aspect, an anchor assembly for engaging a connecting element along the spinal column includes an anchor member engageable to a vertebral body, a receiver at a proximal end of the anchor member and an engaging member. The receiver defines a passage for receiving the connecting element therethrough and an internal thread profile extending from the passage. The engaging member includes a rotational center and an end surface having a plurality of elongated, arcuate projecting members extending therefrom about the rotational center. The projecting members are structured to deform an outer surface of the connecting element when threadingly engaged to the internal thread profile of the receiver in contact with the connecting element.

According to an aspect, a spinal implant assembly includes an anchor member, a receiver at a proximal end of the anchor member defining a passage for receiving a connecting element therethrough and an internal thread profile extending from the passage. An engaging member is threadingly engageable with the internal thread profile of the receiver. The engaging member includes a rotational center and an end surface having a plurality of elongated, arcuate projecting members extending therefrom about the rotational center. The projecting members engage an outer surface of the connecting element when the engaging member is threadingly engaged to the internal thread profile of the receiver. A first one of the plurality of projecting members includes a first height extending from the end surface and a second one of the projecting members includes a second height extending from the end surface. The first height is greater than the second height.

These and other aspects will be discussed further below.

DESCRIPTION OF THE ILLUSTRATED EMBODIMENTS

Figure 1:
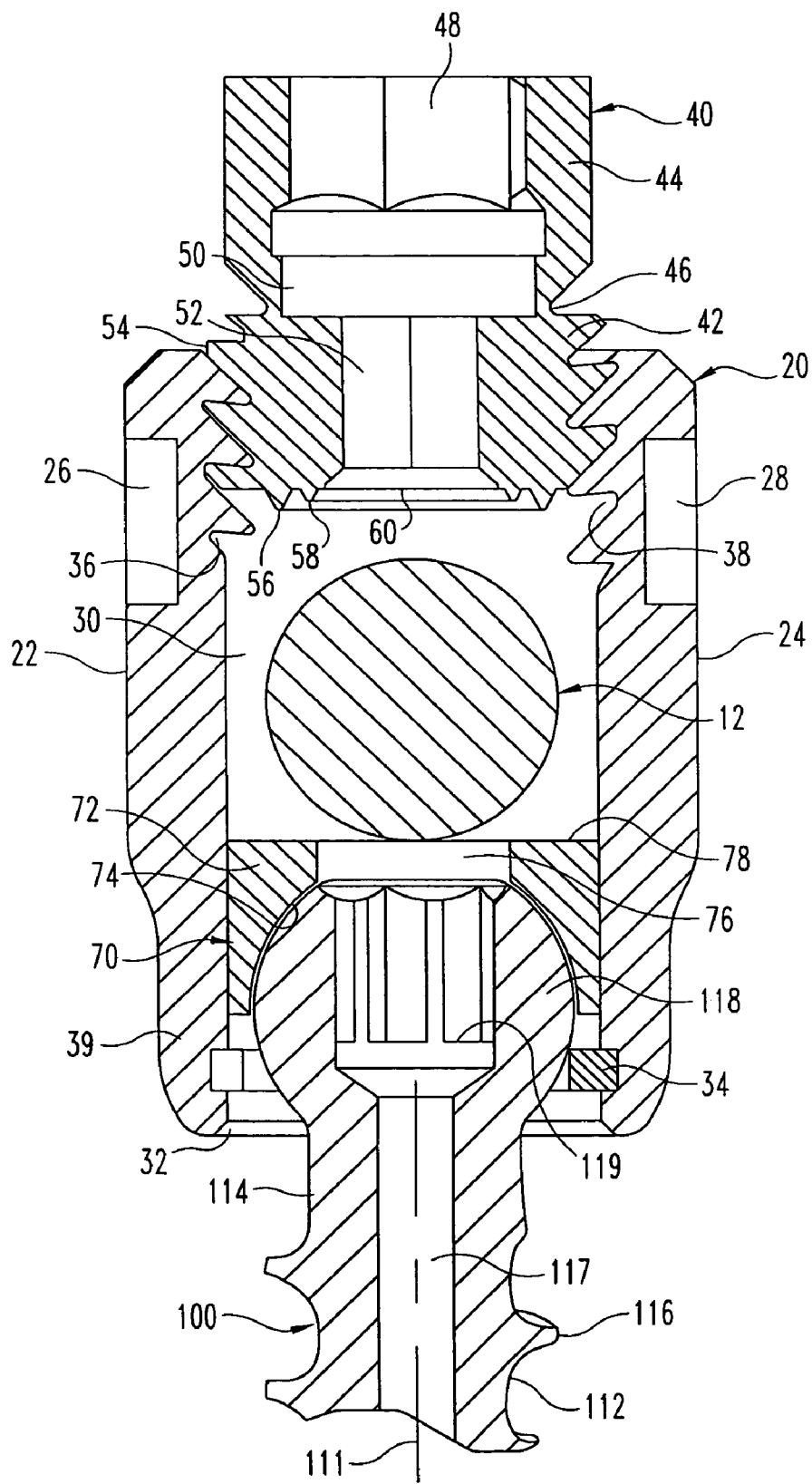
FIG. 1 is a section view of a portion of an anchor assembly with a connecting element.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Devices and methods for securing a connecting element in an anchor assembly are provided for spinal and other bone stabilization surgical procedures. The anchor assembly includes an engaging member with a plurality of distal projecting members to penetrate, deform, bite into, interrupt, interfit or interdigitate with the outer surface of the connecting element to securely engage the connecting element when the engaging member is engaged to the receiver of the anchor assembly. The plurality of projecting members can be elongated and arcuate so as to extend at least partially about a rotational center of the engaging member.

In one embodiment, at least one of the projecting members has a height extending from a distal end surface of the engaging member that is greater than a height of a second one of the projecting members. In another embodiment, the projecting members form concentric rings about the rotational center of the engaging member. In yet another embodiment, one of the projecting members extends about a portion of the engaging member on one side of its rotational center and another projecting member extends about a portion of the engaging member on another side of the rotational center opposite the one side. The projecting members can have differing heights extending from the distal end surface to facilitate multi-location engagement with the outer surface of the connecting element, even if the connecting element is contoured or flexed in the receiver.

Referring to FIG. 1, there is shown a sectional view of a portion of an anchor assembly 10. Anchor assembly 10 includes an elongated connecting element 12 positioned through a passage 30 of a receiver 20. Receiver 20 is joined to an anchor member 100 extending distally therefrom. Engaging member 40 is engaged to receiver 20 and movable therealong to contact connecting element 12 to secure it in receiver 20 with anchor member 100 engaged to an underlying bony structure.

Receiver 20 includes a pair of arms 22, 24 extending generally parallel to one another and defining passage 30 therebetween. Arms 22, 24 can include internal thread profiles 36, 38, respectively, to threadingly engage engaging member 40. Arms 22, 24 can also include external recesses 26, 28, respectively, to provide locations for tools to grasp receiver 20 and/or anchoring assembly 10 during surgery. Arms 22, 24 extend proximally from a lower bowl portion 39 which pivotally houses a proximal head portion 118 of anchor member 100. Bowl portion 39 defines a distal opening 32 in communication with passage 30, and anchor member 100 extends through distal opening 32. A retaining member 34 can axially retain anchor member 100 in receiver 20 without letting head portion 118 pass through distal opening 32. Retaining member 34 can be a separate component from receiver 20, such as a split ring, or can be formed as an integral portion of receiver 20, such as a flange or a lip about distal opening 32.

A seat member 70 can be provided adjacent to head portion 118 of anchor member 100 between connecting element 12 and head portion 118. Seat member 70 includes a body 72 having a concavely curved lower surface 74 for receiving head portion 118, and an opposite seating surface 78 against which connecting element 12 can be secured. Seat member 70 can also include a central aperture 76 through which a driving tool can beH positioned to engage head portion 118 and secure anchor member 100 to bony structure. Seating surface 78 can be flat, as shown, or can include a concave curvature or other shape to at least partially receive connecting element 12 therein.

Engaging member 40 includes a first portion 42 for engaging receiver 20 and a second portion 44 extending proximally from first portion 42. Embodiments without second portion 44 are also contemplated, and could be configured such as shown with engaging member 40' in FIG. 5. In the illustrated embodiment, first portion 42 includes a cylindrical body with an external thread profile 54 configured to threadingly engage thread profiles 36, 38 along arms 22, 24. Second portion 44 can be configured like a cylindrical head or end member with a smooth outer surface and a proximal, inner tool recess 48 extending axially therethrough along a central rotational axis 41 of engaging member 40. Proximal tool recess 48 can receive a driving tool (not shown) and facilitate application of rotational forces to engage engaging member 40 firmly against connecting element 12. A break-off region 46 between first and second portions 42, 44 can be provided to allow second portion 44 to be removed, leaving only first portion 42 engaged to the receiver, such as shown with respect to engaging member 40' in FIG. 5.

First portion 42 can also include an inner, distal tool recess 52 extending axially therethrough about rotational center 41. Distal tool recess 52 can be engaged by a tool to allow further tightening or removal of first portion 42 when engaged to arms 22, 24. Distal tool recess 52 can be smaller in cross-sectional size so that a driving tool sized to engage proximal tool recess 48 cannot pass into distal tool recess 52, facilitating severing of second portion 44 from first portion 42. However, a continuously sized tool recess between portions 42, 44 is not precluded. In the illustrated embodiment, a cylindrical recess portion 50 is provided between proximal tool recess 48 and distal tool recess 52. Recess portion 50 can be located adjacent to or along break-off region 46, providing a uniform wall thickness about break-off region 46 that facilitates removal of second portion 44 from first portion 42 when sufficient torque is applied. The threshold torque can be controlled or varied by controlling or varying the wall thickness at break-off region 46 during manufacture of engaging member 40.

Recesses 48, 52 can include any suitable configuration for engagement with a driving tool to deliver driving forces to engaging member 40, including a hex shape, star shape, cross-shape, slotted shape, or other non-circular shape. Other embodiments contemplate one or more of the tool recesses 48, 52 could be omitted, and engaging member 40 could be configured for external engagement by a tool.

Figure 4:
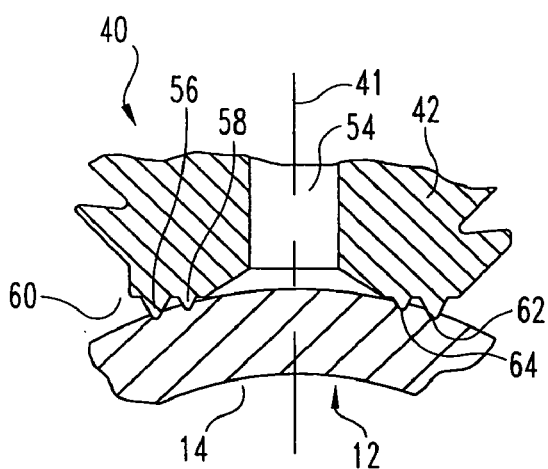
FIG. 4 is a sectional view along the rotational axis of a distal part of the first portion of the engaging member of FIG. 2 with the engaging member engaged to a contoured connecting element.

First portion 42 includes a distal end surface 60 positionable against connecting element 12 in passage 30 of receiver 20. Distal tool recess 52 can open through distal end surface 60, although such is not required. First portion 42 further includes a first projecting member 56 and a second projecting member 58 extending distally from distal end surface 60. As shown in FIG. 4, projecting members 56, 58 can engage the outer surface 14 of connecting element 12 to firmly grip engaging member 40 to connecting element 12. Projecting members 56, 58 can resist slippage of connecting element 12 relative to receiver 20 in at least the direction along which passage 30 extends when engaged to connecting element 20.

Figure 2:
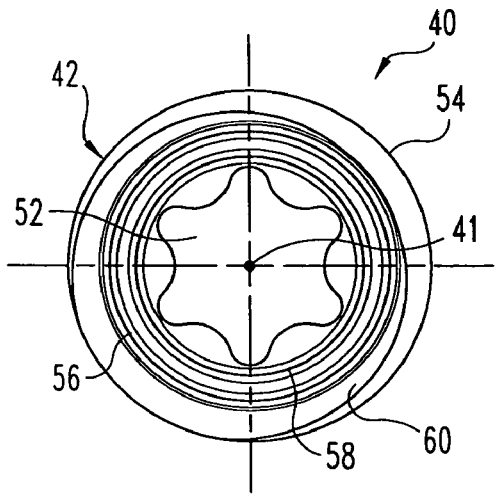
FIG. 2 is an end view of an engaging member of the anchor assembly of FIG. 1.
Figure 3:
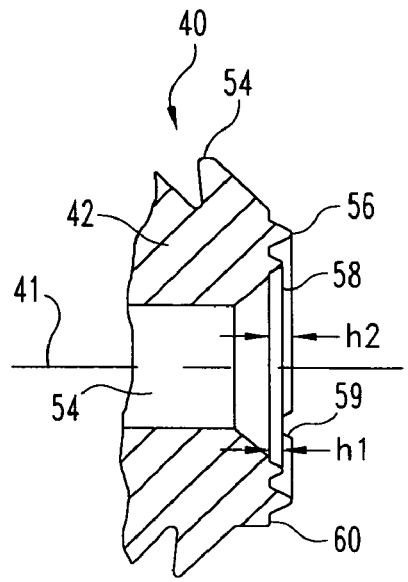
FIG. 3 is a sectional view along the rotational axis of a distal part of a first portion of the engaging member of FIG. 2.

As further shown in FIG. 2, projecting members 56, 58 can extend about rotational center 41 of engaging member 40, forming concentric rings that extend completely or substantially completely about center 41. Projecting members 56, 58 can further extend about distal tool recess 52 opening through end surface 60. It is contemplated that the projecting members can include interruptions along their respective lengths, such as the notch 59 shown in FIG. 3. However, it is contemplated that the projecting members 56, 58 are each substantially continuous along their respective lengths.

As shown in FIGS. 1-4, projecting members 56, 58 can include a cross-section along their respective lengths that is defined by a V-shape that tapers distally away from end surface 60 to an outer end 62, 64, respectively. Projecting members 56, 58 can include a base portion opposite the respective outer end 62, 64 integrally formed with first portion 42 at distal end surface 60. Furthermore, first projecting member 56 can include a height h1 extending distally from distal end surface 60 that is less than a height h2 of a second projecting member 58 extending from distal end surface 60. The variation in height facilitates engagement of the projecting members 56, 58 with a connecting element 12 that may be contoured, curved, bowed or otherwise non-linear in passage 30 of anchor assembly 10. Outer ends 62, 64 can be pointed to form an elongate pint or edge along the respective projecting member 56, 58. Other configurations for outer ends 62, 64 are also contemplated.

For example, as shown in FIG. 4, the longitudinal portion of connecting element 12 is shown bowed such that a convex side of connecting element 12 is oriented toward engaging member 40. When distal end surface 60 contacts the apex or other portion of the curved connecting element 12, further advancement of engaging member 40 into receiver 20 is not readily attainable due to the resistance provided by connecting element 12. It should be understood that all or a portion of connecting element 12 could be non-compressible, substantially non-compressible, or compressible. It should be understood that engaging member 40 can be employed with non-curved or linear connecting elements.

When distal end surface 60 contacts connecting element 12 adjacent rotational center 41, further advancement of engaging member 40 is resisted. Projecting member 56 closest to center 41 can be substantially embedded into or otherwise in substantial contact with connecting element 12. Since projecting member 58 is positioned farther away from rotational center 41 where it contacts the apex of connecting element 12, a projecting member having the same height as projecting member 56 may not engage or sufficiently engage connecting element 12 since, in the illustrated embodiment, connecting element 12 curves away from rotational center 41 and distal end surface 60. However, the greater height of projecting member 58 allows it to embed or otherwise substantially engage connecting element 12 even when distal end surface 60 contacts connecting element 12 at rotational center 41. Furthermore, by providing projecting members about rotational center 41 of engaging member 40, portions of the projecting members 56, 58 can always be aligned with connecting element 12 in passage 30 for contact with connecting element 12 no matter the rotational position of engaging member 40 relative to connecting element 12.

FIGS. 6-10 show another embodiment engaging member 140 that can be similar to engaging member 40, but includes another embodiment projecting structure extending from distal end surface 160 thereof. Engaging member 140 includes a distal first portion 142 having an external thread profile and a proximal second portion 144 that can provide a head removably joined at a break-off region 146 to first portion 142. Engaging member 140 includes an intermediate portion 143 between first portion 142 and second portion 144. Second portion 144 defines a proximal tool recess 148 and first portion 142 defines a distal tool recess 152. A cylindrical recess portion 150 can extend between tool recesses 148, 152 adjacent break-off region 146. The tool recesses and break-off region can be structured substantially as discussed above with respect to engaging member 40.

First portion 142 includes a distal end surface 160 having a first projecting member 156 extending along end surface 160 partially about a rotational center 141 of engaging member 140. First portion 142 also includes a second projecting member 158 extending along end surface 160 partially about rotational center 141. Projecting members 166, 168 extend in substantially non-overlapping relation about rotational center 141 and, in the illustrated embodiment, tool recess 152 opening in end surface 160. First projecting member 156 is located to a first side of rotational center 141 and second projecting member 158 is located to a second side of rotational center 141 opposite the first side. In the illustrated embodiment, projecting members 156, 158 extend no more than halfway about rotational center 141. First projecting member 156 can include an end wall 169 that is spaced from an adjacent end wall 167 of projecting member 158, and the opposite ends 168, 166 of projecting members 156, 158 are positioned in nearly radial alignment with one another about rotational center 141.

In the illustrated embodiment, each of the first and second projecting members 156, 158 extends along an arc defined by a radius extending from rotational center 141. First projecting member 156 can be located closer to rotational center 141 than second projecting member 158, i.e. can be defined by an arc of lesser radius from rotational center 141. Other embodiments contemplate that one or both of the projecting members 156, 158 extend along a non-circular path about center 141, such as an oval or elliptical path, or that the path includes of each can include linear and/or curved segments. Other spatial arrangements relative to center 141 are also contemplated.

First projecting member 156 can include a height h3 extending from distal end surface 160 to an outer end 162, and second projecting member 158 can include a height h4 extending from distal end surface 160 to an outer end 164. Height h4 can be greater than height h3. The varying heights projecting members 156, 158 from distal end surface 160 and the variable spacing from rotational center 141 can provide the ability to enhance engagement of a contoured or flexed connecting element as discussed above with respect to engaging member 40. The outer ends 162, 164 can be truncated to provide a flat surface profile along the respective projecting member 156, 158 to prevent the formation of sharp points that may break-off in situ. However, the use of a sharp, elongated point or edge along outer ends 162, 164 is not precluded.

Projecting members 156, 158 can include end walls that are inclined or sloped to facilitate rotation of engaging member 140 against connecting element 12 without the end wall catching or hanging up on connecting element 12. For example, projecting member 158 includes trailing end wall 167 having a sloped surface that extends from distal end surface 160 to outer end 164 of projecting member 158. The leading end 166 of projecting member 158 and leading end 169 of projecting member 156 can also be sloped to accommodate disengagement of engaging member 140 from connecting element 12. Leading end 169 of projecting member 156 can be aggressively sloped and form a cutting edge to facilitate entry of projecting member 156 into connecting element 12. Trailing end 168 of projecting member 156 can run-out into projecting member 158 adjacent its leading end 166. While limited overlapping of projecting members 156, 158 is contemplated, projecting members 156, 158 extend around rotational center 141 in substantially non-overlapping relation.

As shown in FIG. 1, anchor member 100 can be a bone screw having proximal head portion 118 and an elongated shaft 112 (only a proximal portion shown in FIG. 1) extending distally from head portion 118 along a longitudinal axis 111. Shaft 112 can include an external thread profile 116, and can also include a lumen 117 extending axially therealong as shown. Shaft 112 can also be solid without a lumen. Lumen 117, if provided, opens into a tool recess 119 opening proximally in head portion 118 to receive a driving tool to facilitate driving anchor member 100 into a bony structure, such as a vertebral body. Head portion 118 can be pivotally captured in receiver 20 with retaining member 34. The pivotal arrangement allows the multi-axial anchor member to be positioned relative to the receiver and connecting element at various angles relative to one another. Such variable positioning can facilitate placement of the connecting element into receiver 20 even when the anatomical conditions prohibit or make difficult a linear arrangement of the connecting element between anchor assemblies. The engaging members 40, 40' 140 can enhancement engagement of the connecting element 12 even if connecting element 12 is contoured through the receiver 20 to accommodate the patient's anatomy.

Figure 5:
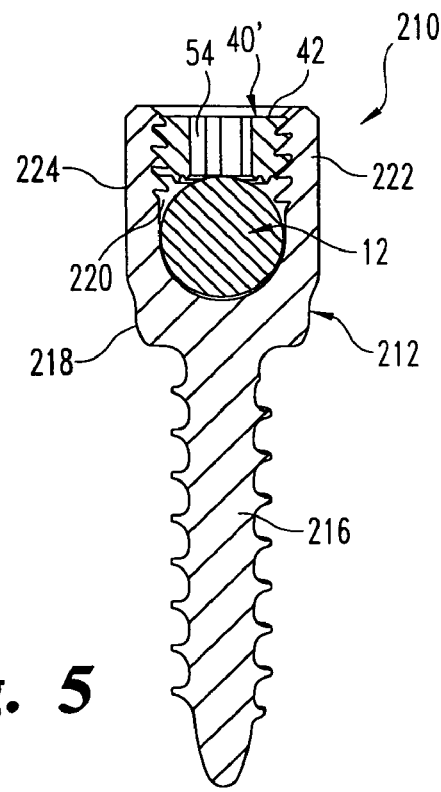
FIG. 5 is a sectional view showing the first portion of the engaging member engaged to a connecting element in another embodiment anchor assembly.
Figure 6:
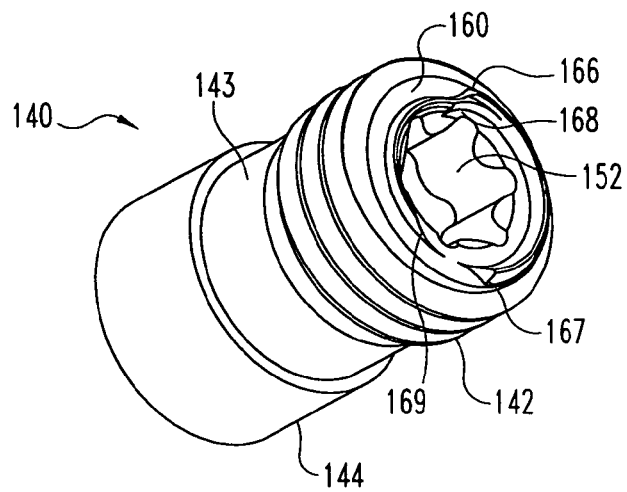
FIG. 6 is a perspective view of another embodiment engaging member engageable to a connecting element in an anchor assembly.
Figure 7:
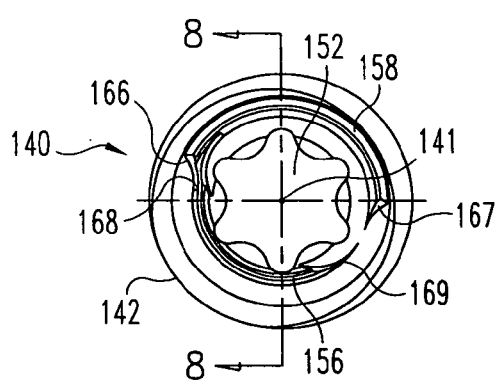
FIG. 7 is an end view of the engaging member of FIG. 6.
Figure 8:
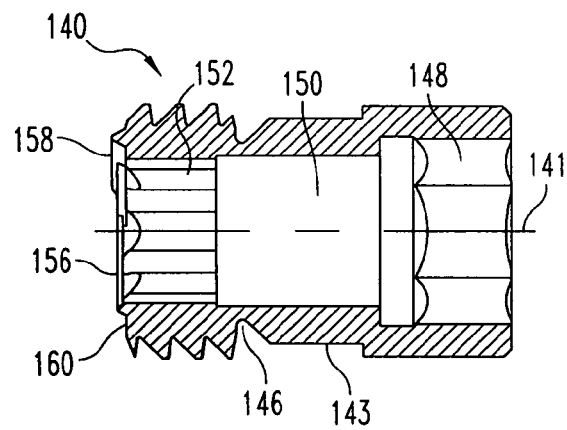
FIG. 8 is a sectional view along line 8-8 of FIG. 7.
Figure 9:
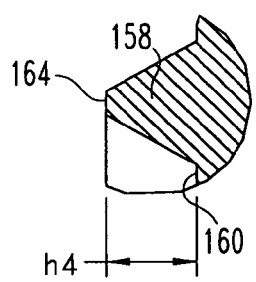
FIG. 9 is a detailed sectional view of a first distal projecting member of the engaging member of FIG. 6.
Figure 10:
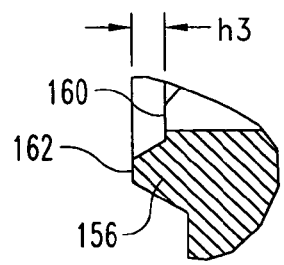
FIG. 10 is a detailed sectional view of a second distal projecting member of the engaging member of FIG. 6.

The anchor assemblies discussed herein can be multi-axial, as shown in FIG. 1, or uni-axial, such as shown in FIG. 5. The uni-axial anchor assemblies provide a fixed positioning of the receiver relative to the anchor member. In FIG. 5, anchor assembly 210 includes an anchor member 212 with an externally threaded shaft 216 integrally formed or structured with a receiver member 218. Receiver member 218 includes arms 222, 224 that form passage 220 to receive connecting element 12 therethrough. Connecting element 12 can seat against the bottom of receiver 218 in passage 220. Arms 222, 224 can be internally threaded to threadingly engage engaging member 40, 40' or 140 in engagement with connecting element 12.

Other embodiments contemplate other forms for the anchoring member. In other embodiments, the distal anchor member can be in the form of a hook, staple, cable, tether, suture anchor, interbody fusion implant, artificial disc implant, bolt, or other structure engageable to bony tissue. The receiver defines a passage that receives a connecting element, such as a rod, tether, wire, cable, plate or other elongated linking member that can extend between one or more additional anchor assemblies secured to one or more additional vertebrae or other bony structure.

The anchor members can be configured as pedicle screws, bolts or other member sized and configured for engaging a pedicle of vertebra. The anchor member can also be configured to engage other parts of a vertebra, or other bony structures in the patient. Furthermore, a set screw, washer, crown, cap or other device may be provided in addition to engaging member 40, 40', 140 for engagement within and/or about receiver 20 to secure connecting element 12 thereto.

Receiver 20 can be configured to receive connecting element 12 in passage 30 with connecting element 12 top-loaded into receiver 20 or loaded into receiver 20 in an end-wise manner. Alternatively, the receiver can be configured so that the connecting element can be side-loaded or bottom loaded therein prior to engagement with engaging member 40, 40', 140. Furthermore, connecting element 12 can be engaged to two or more anchor assemblies 10, 210 along the spinal column, and provide stabilization for multiple spinal motion segments. The connecting element can also be positioned for engagement with a single anchor assembly 10, 210 engaged to the spinal column, or for procedures involving single vertebra.

Connecting element 12 can be a spinal rod connectable to one or more anchor assemblies to rigidly stabilize the spinal column. Connecting element 12 can also be flexible to allow motion of the spinal motion segment or segments to which it is attached. It is also contemplated that connecting element 12 can comprise multiple components. Various forms for the connecting element 12 are contemplated, including plates, wires, struts, cables, and other devices capable of engagement in a receiver of an anchor assembly with engaging members 40, 40', 140. Connecting element 12 can be a spinal rod comprised of any one or combination of metal, metal allow, plastic, polymer, tissue, fabric, or mesh material, for example.

While the invention has been illustrated and described in detail in the drawings and foregoing description, the same is to be considered as illustrative and not restrictive in character. All changes and modifications that come within the spirit of the invention are desired to be protected.

What is claimed is:

1. An anchor assembly for engaging a connecting element along the spinal column, comprising:
    an anchor member engageable to a vertebral body; a receiver at a proximal end of said anchor member, said receiver defining a passage for receiving the connecting element therethrough and an internal thread profile extending from said passage; and
    an engaging member threadingly engageable with said internal thread profile, wherein said engaging member includes a rotational center and an end surface having a plurality of elongated, arcuate projecting members extending therefrom about said rotational center, said projecting members being structured to deform an outer surface of said connecting element when said engaging member is threadingly engaged to said internal thread profile of said receiver with said projecting members in contact with the connecting element, wherein a first one of said projecting members extends partially about said rotational center on a first side of said rotational center along an arc having a first radius from said rotational center of said engaging member and a second one of said projecting members extends partially about said rotational center on a second side of said rotational center along an arc having a second radius from said rotational center of said engaging member and opposite said first side and in substantially non-overlapping relation with said first projecting member with a part of said first projecting member overlapping with a part of said second projecting member, wherein said first projecting member includes a first height extending from said end surface and said second projecting member includes a second height extending from said end surface, said first height being greater than said second height and said first radius being greater than said second radius, wherein said first projecting member and said second projecting member each include a leading end wall formed by a sloped surface extending from said end surface to an outer end of said respective projecting member with said leading end wall of at least one of said first and second projecting members forming a cutting edge to facilitate entry of said at least one of said first and second projecting members into the connecting element as said engaging member is threadingly engaged to said internal thread profile of said receiver and said outer end is continuous and arcuate from said leading end wall along a length of said at least one of said first and second projecting members.

2. The assembly of claim 1, wherein said engaging member includes a first portion having a cylindrical body with external threads extending thereabout and a second portion extending from said first portion, wherein said second portion is severable from said first portion upon application of a threshold torque to said second portion relative to said first portion.

3. The assembly of claim 2, wherein said first portion includes a first tool recess about said rotational center configured to engage a driving tool and said second portion includes a second, larger tool recess about said rotational center and in axial communication with said first tool recess.

4. The assembly of claim 1, wherein said connecting element is a flexible spinal rod.

5. The assembly of claim 1, wherein each of said first and second projecting members includes a generally V-shaped cross-sectional profile transversely to a length thereof, said V-shaped profile having a base integrally formed with said end surface and tapering away from said end surface to said outer end of said projecting member opposite said base.

6. The assembly of claim 5, wherein said outer end of each of said projecting members is pointed to form an elongated peak along said projecting member.

7. The assembly of claim 1, wherein said first projecting member and said second projecting member each extend no more than halfway about said rotational center.

8. The assembly of claim 1, wherein said engaging member includes an internal tool recess that extends through said engaging member along said rotational center, said internal tool recess opening at an end opposite said end surface and opening at said end surface thereof and said projecting members extend about said tool recess.

9. The assembly of claim 1, wherein said first projecting member and said second projecting member each include a trailing end wall opposite said leading end wall thereof, said trailing end walls each being formed by a sloped surface extending from said end surface to said outer end of said respective projecting member with said first and second projecting members extending about said rotational center from said leading end wall to said trailing end wall thereof.

10. The assembly of claim 1, wherein said first and second projecting members each include a generally V-shaped cross-sectional profile transversely to a length thereof, said profile tapering away from said end surface to said outer end, said outer ends each being truncated to provide a flat surface profile along said respective projecting member.

11. A spinal implant assembly, comprising: an anchor member engageable to a vertebral body;
a receiver at a proximal end of said anchor member, said receiver defining a passage and an internal thread profile extending from the passage;
an elongated connecting element in said passage of said receiver, said connecting element being structured for positioning along at least two vertebrae of a spinal column; and
an engaging member threadingly engageable with said internal thread profile of said receiver, wherein said engaging member includes a rotational center a first end and an end surface opposite said first end having a plurality of elongated, arcuate projecting members extending therefrom about said rotational center, said projecting members engaging an outer surface of said connecting element when threadingly engaged to said internal thread profile of said receiver, wherein a first one of said plurality of projecting members extends along an arc having a first radius from said rotational center and said first projecting member includes a first height extending from said end surface and a second one of said projecting members extends along an arc having a second radius from said rotational center and said second projecting member includes a second height extending from said end surface, wherein said second projecting member extends in substantially non-overlapping relation with said first projecting member with a part of said first projecting member overlapping with a part of said second projecting member, wherein said first height is greater than said second height and said first radius is greater than said second radius, said second projecting member further including a leading end wall extending from said end surface of said engaging member to an outer end of said second projecting member, said leading end wall forming a cutting edge to facilitate entry of said second projecting member into said connecting element as said second projecting member engages said connecting element, said outer end of said second projecting member further being continuous and arcuate from said leading end wall along a length of said second projecting member, said engaging member further including a tool recess extending therethrough that opens at said end surface and at said first end.

12. The assembly of claim 11, wherein said plurality of projecting members includes first and second projecting members that each form a generally a V-shaped cross-sectional profile transversely to a length thereof, said profile tapering away from said end surface to an outer end spaced from said end surface.

13. The assembly of claim 12, wherein said first projecting member extends partially about said rotational center on a first side of said rotational center of said engaging member and said second projecting member extends partially about said rotational center on a second side of said rotational center of said engaging member.

14. The assembly of claim 13, wherein said first and second projecting members each include an end wall extending from said outer end of said respective projecting member along a sloped surface to said end surface of said engaging member.

15. The assembly of claim 12, wherein:
said first height is substantially constant along a substantial length of said first projecting member; and
said second height is substantially constant along a substantial length of said second projecting member.

16. The assembly of claim 11, wherein said engaging member includes a proximal break-off portion and a distal portion having a cylindrical body with external threads, said projecting members extending from said distal portion.

17. The assembly of claim 11, wherein said first projecting member and said second projecting member each extend no more than halfway about said rotational center.

18. The assembly of claim 11, wherein said first projecting member includes a leading end wall and an opposite trailing end wall, said leading and trailing end walls each being formed by a sloped surface extending from said end surface to an outer end of said first projecting member with said first projecting member extending about said rotational center from said leading end wall to said trailing end wall thereof.

19. The assembly of claim 11, wherein said first and second projecting members each include a generally V-shaped cross-sectional profile transversely to a length thereof, said profile tapering away from said end surface to an outer end, said outer ends each being truncated to provide a flat surface profile along said respective projecting member.

* * * * *